United States Patent
Gu et al.

(10) Patent No.: US 9,745,264 B2
(45) Date of Patent: Aug. 29, 2017

(54) METHOD FOR PREPARING SILODOSIN AND INTERMEDIATE THEREOF

(71) Applicants: SHANGHAI SYNCORES TECHNOLOGIES, INC., Shanghai (CN); ZHEJIANG HUAHAI PHARMACEUTICALS CO., LTD., Zhejiang (CN)

(72) Inventors: Hong Gu, Shanghai (CN); Jian Cao, Shanghai (CN); Liushan Chen, Shanghai (CN); Luning Huang, Shanghai (CN)

(73) Assignees: Shanghai Syncores Technologies, Inc., Shanghai (CN); Zhejiang Huahai Pharmaceuticals Co., Ltd., Zhejiang (CN)

( * ) Notice: Subject to any disclaimer, the term of this patent is extended or adjusted under 35 U.S.C. 154(b) by 0 days.

(21) Appl. No.: 15/103,195

(22) PCT Filed: Oct. 20, 2014

(86) PCT No.: PCT/CN2014/088953
§ 371 (c)(1),
(2) Date: Jun. 9, 2016

(87) PCT Pub. No.: WO2015/085827
PCT Pub. Date: Jun. 18, 2015

(65) Prior Publication Data
US 2016/0304452 A1    Oct. 20, 2016

(30) Foreign Application Priority Data
Dec. 9, 2013 (CN) .......................... 2013 1 0659145

(51) Int. Cl.
*C07D 209/08* (2006.01)
*C07C 51/41* (2006.01)
*C07C 59/255* (2006.01)
*C07C 303/32* (2006.01)
*C07C 309/25* (2006.01)

(52) U.S. Cl.
CPC ............ *C07D 209/08* (2013.01); *C07C 51/41* (2013.01); *C07C 59/255* (2013.01); *C07C 303/32* (2013.01); *C07C 309/25* (2013.01); *C07C 2602/42* (2017.05)

(58) Field of Classification Search
CPC .................................................... C07D 209/08
See application file for complete search history.

(56) References Cited

FOREIGN PATENT DOCUMENTS

| CN | 101993406 | 3/2011 |
|---|---|---|
| WO | 2012/062229 | 5/2012 |

OTHER PUBLICATIONS

International Search Report for PCT/CN2014/088953; Jan. 28, 2015.
Written Opinion of the International Search Authority for PCT/CN2014/088953; Jan. 28, 2015.

*Primary Examiner* — Shawquia Jackson
(74) *Attorney, Agent, or Firm* — Calfee, Halter & Griswold LLP

(57) ABSTRACT

Provided is a method for preparing silodosin. Also provided is a method for preparing an organic acid salt of a new intermediate 3-(7-cyano-5-((R)-2-((R)-1-phenylethylamino)propyl)-1-hydrogen-indolyl) propyl alcohol (ester or ether), and a new intermediate 3-(7-cyano-5-((R)-2-(((R)-1-phenethyl)(2-(2-(trifluoroethoxy)phenoxy) ethyl)amino)propyl) 1-hydrogen-indolyl)propyl alcohol (ester or ether) and a salt thereof. The method has the following advantages: raw materials are cheap and easy to obtain, the operation is simple, the intermediate and product are easy to purify, the yield is high, and the method is applicable to industrial production.

11 Claims, No Drawings

METHOD FOR PREPARING SILODOSIN AND INTERMEDIATE THEREOF

CROSS-REFERENCE TO RELATED APPLICATIONS

This application is a National Phase Application of International Application PCT/CN2014/088953, with an international filing date of Oct. 20, 2014, which is based on and claims priority to Chinese Patent Application No. 201310659145.8, filed on Dec. 9, 2013, the entire contents of which are incorporated herein by reference.

FIELD OF THE INVENTION

The present invention relates to the field of pharmaceutical chemistry, specifically to a method of preparing a medicament silodosin for treating prostatic hyperplasia. Meanwhile, the present invention further relates to the key intermediates for synthesizing silodosin, organic acid salts of 3-(7-cyano-5-((R)-2-((R)-1-phenylethylamino)propyl)-1-H-indolyl)propyl alcohol (ester or ether), and 3-(7-cyano-5-((R)-2-(((R)-1-phenylethyl)(2-(2-(trifluoroethoxy)phenoxy)ethyl)amino)propyl)-1-H-indolyl)propyl alcohol (ester or ether) and its salts, as well as to methods of preparing the two intermediates.

BACKGROUND OF THE INVENTION

Silodosin has selective inhibition on the contraction of urethral smooth muscle and reduces the pressure in the urethra, but silodosin does not greatly influence on the blood pressure, thus it is used for treating benign prostatic hyperplasia.

As an efficient method of producing silodosin, the patent CN101993406 reports the following route:

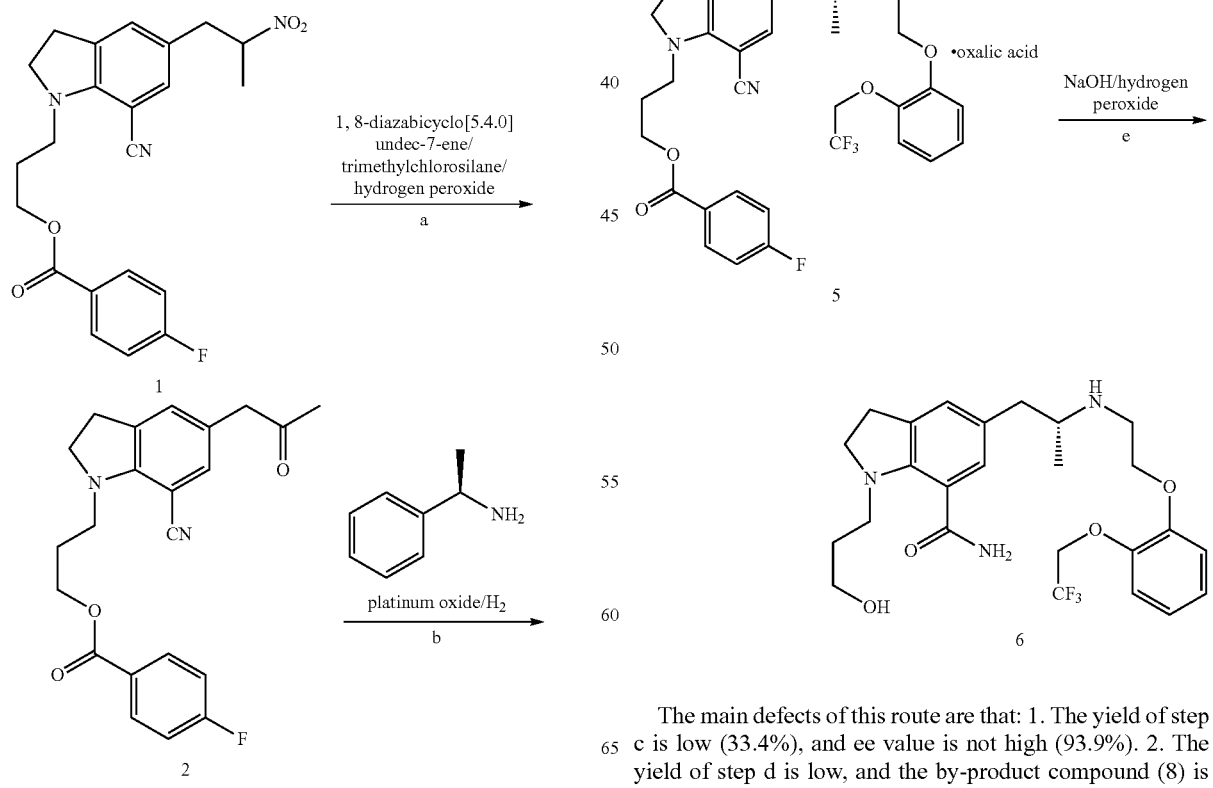

The main defects of this route are that: 1. The yield of step c is low (33.4%), and ee value is not high (93.9%). 2. The yield of step d is low, and the by-product compound (8) is difficult to be removed in the purification process.

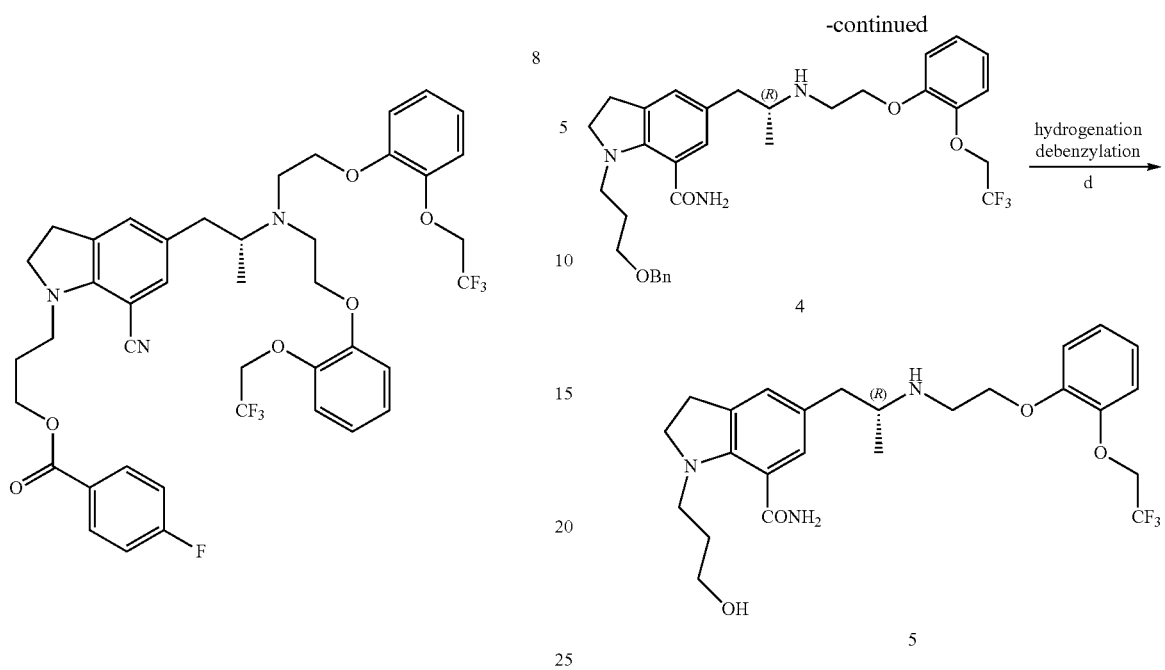

As another efficient method of producing silodosin, the patent WO2012062229 reports the following route:

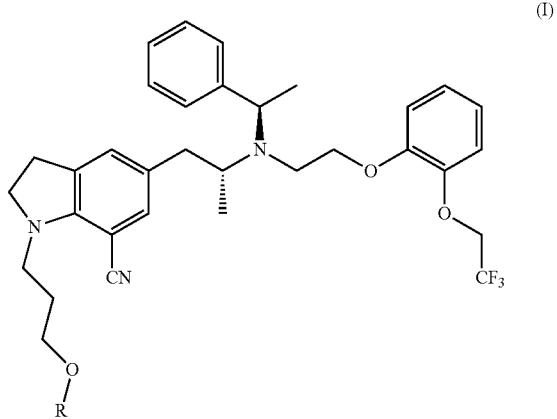

to This route mainly has two defects: 1. The reaction paths are long. 2. The reaction yield of step a is low (44.8%), and column chromatography is required for purification.

SUMMARY OF THE INVENTION

In order to overcome the defects of multiple processing steps and low yield for preparing silodosin in the prior art, the present invention is proposed. The present application mainly provides a route of synthesizing silodosin. Meanwhile, the present application further provides two new intermediate compounds and their salts for synthesizing silodosin, and the corresponding preparation methods.

In one aspect, the present invention relates to two new intermediate compounds (I) and (II) for preparing silodosin.

To be specific, the present invention provides the intermediate compounds (I) and (II) comprising:

3-(7-cyano-5-((R)-2-(((R)-1-phenylethyl)(2-(2-(trifluoroethoxy)phenoxy)ethyl)amino)propyl)-1-H-indolyl)propyl alcohol (ester or ether) as represented by structural formula (I), and its pharmaceutically acceptable salts, (I)

wherein, R is H, formyl, aliphatic acyl, substituted or unsubstituted aromatic formyl, tetrahydropyranyl or trialkylsilicyl, and so on. Preferably, R is 4-fluorobenzoyl.

Structural formula (II):

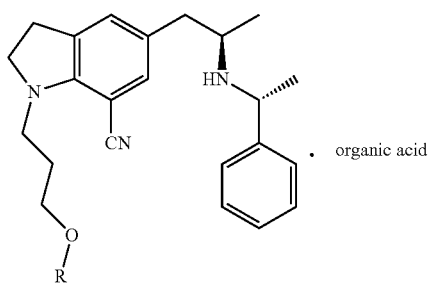

(II)

· organic acid wherein, R is H, formyl, aliphatic acyl, substituted or unsubstituted aromatic formyl, tetrahydropyranyl or trialkylsilicyl and so on, preferably 4-fluorobenzoyl. The organic acid can selected from L-dibenzoyl tartaric acid, L-lactic acid, L-malic acid, R-camphorsulfonic acid, S-mandelic acid, N-carbobenzoxy-L-phenylalanine, L-tartaric acid and so on, preferably R-camphorsulfonic acid or L-tartaric acid.

In the second aspect, the present invention provides the methods of preparing compounds (I) and (II) and their salts.

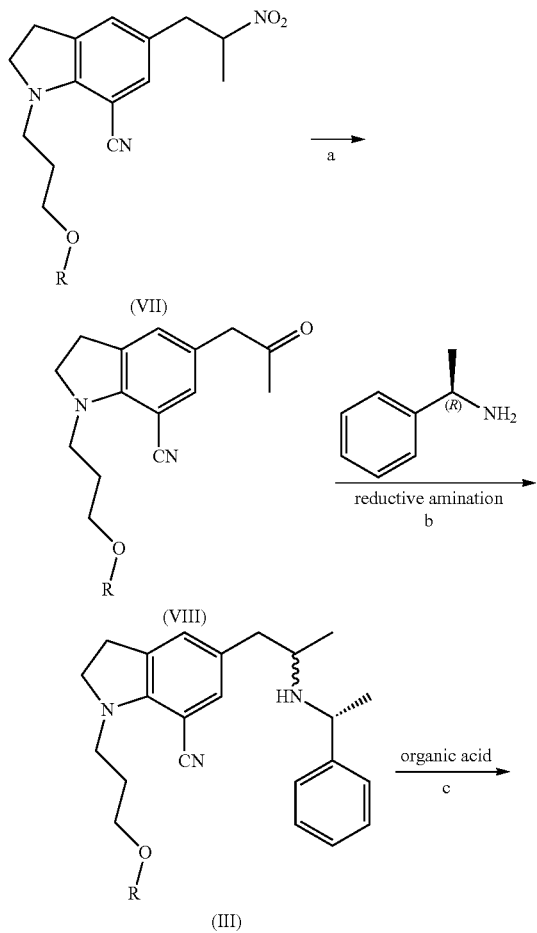

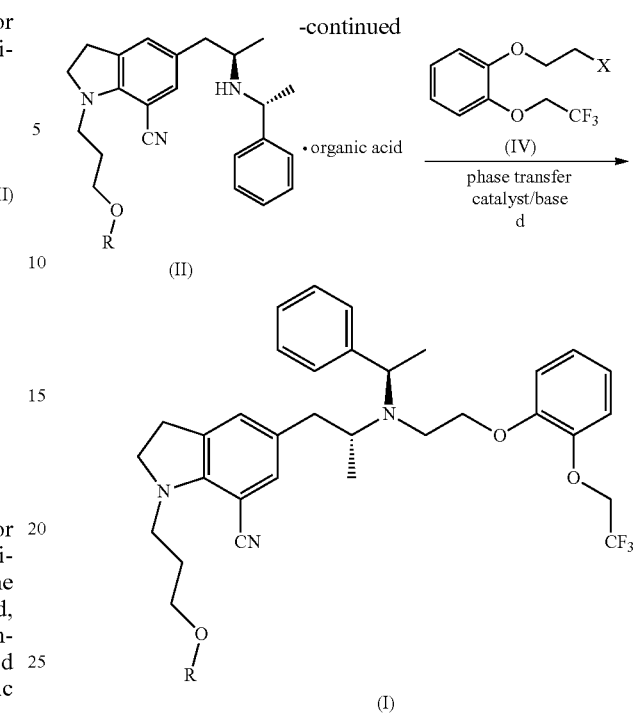

The methods specifically comprise: with reference to the preparation method of the patent CN101993406, compound (VII) firstly reacts with 1,8-diazabicyclo[5.4.0]undec-7-ene, trimethylchlorosilane and hydrogen peroxide to produce compound (VIII), and then reductive amination is conducted between compound (VIII) and R-(+)-α-phenylethylamine to produce compound (III).

Subsequently, compound (III) is reacted with organic acid to produce compound (II), wherein the organic acid is selected from L-dibenzoyl tartaric acid, L-lactic acid, L-malic acid, R-camphorsulfonic acid, S-mandelic acid, N-carbobenzoxy-L-phenylalanine, L-tartaric acid and so on, preferably R-camphorsulfonic acid or L-tartaric acid; the molar ratio of compound (IV): organic acid is 1:(0.8~2.0), preferably 1:(1.0~1.1); the reaction solvent is a single organic solvent selected from dichloromethane, acetone, butanone, ethyl acetate, methanol, ethanol, isopropanol, acetonitrile, tetrahydrofuran, methyl tertiary ether, isopropyl ether and so on, wherein preferably acetone or butanone; and the reaction temperature is 0~80° C.

Afterwards, compound (II) reacts with compound (IV) to produce compound (I), wherein X in compound (IV) is selected from Cl, Br, I and $OSO_2Me$ etc., and preferably Br; the phase transfer catalyst is selected from quaternary ammonium salt or crown ether, e.g., tetrabutylammonium bromide, tetrabutylammonium chloride, tetrabutylammonium hydrogen sulfate, 18-crown-6, 15-crown-5 etc., preferably tetrabutylammonium bromide or 18-crown-6. All of these phase transfer catalysts are common types of phase transfer catalysts in the art. As for the same type of phase transfer catalysts, the structures and reaction mechanisms are substantially the same. The Examples of the present invention have enumerated the most commonly used phase transfer catalysts among the above types. A person skilled in the art, on the basis of the present invention in view of commonly known knowledge in the art, could predict that the other phase transfer catalysts also can achieve the technical solution of the present invention and reach the corresponding technical effect. The base used the above step is inorganic base or organic base, wherein the inorganic base is selected from potassium hydroxide, sodium hydroxide, sodium bicarbonate, potassium bicarbonate, potassium carbonate, sodium carbonate etc., preferably sodium carbonate; the organic base is selected from diisopropyl ethyl amine, triethylamine, 1,8-diazabicyclo[5.4.0]undec-7-ene, pyridine etc., preferably diisopropyl ethyl amine; the molar ratio of compound (II): compound (IV): phase transfer catalyst: base is 1:(1.0~5.0):(0.1~2.0):(1.0~20.0), preferably 1:(1.5~2.5):(0.8~1.5):(3.0~5.0); the reaction can be conducted in the presence of an organic solvent, wherein the organic solvent can be selected from acetonitrile, toluene, xylene, N,N-dimethyl acetamide, N,N-dimethyl formamide, N-methyl pyrrolidone, preferably N-methyl pyrrolidone; in addition, the reaction can be also conducted in the absence of an organic solvent; and the reaction temperature is 25~150° C., preferable 100~130° C.

In the third aspect, the present invention further provides a method of preparing silodosin by using the compound having structural formula (I) as the intermediate, comprising the following two steps:

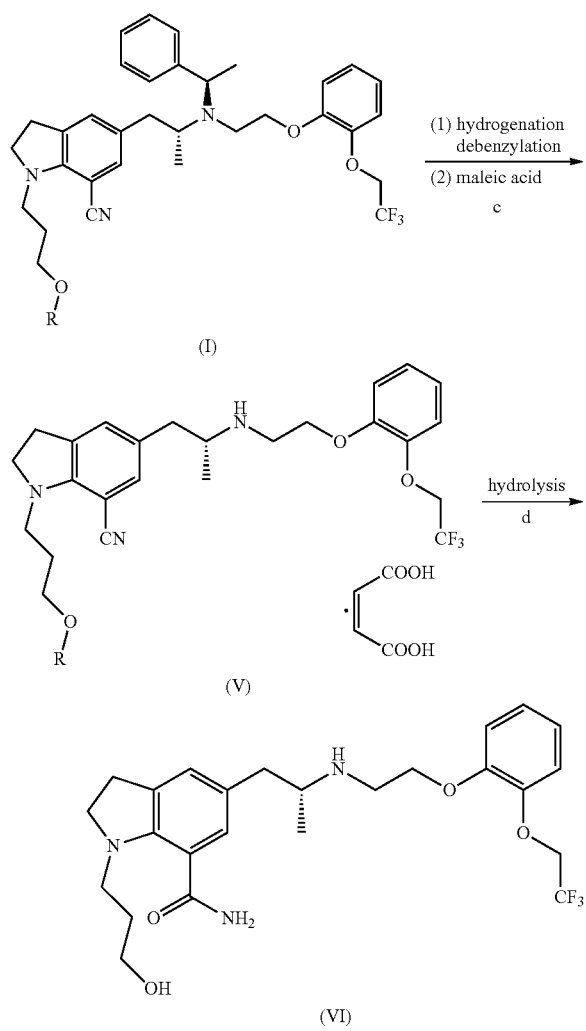

wherein, R is H, alkyl-substituted formyl, substituted or unsubstituted benzoyl, pyranyl or alkylsilicyl and so on, preferably 4-fluorobenzoyl.

The method of preparing silodosin by using compound (I) is:

1) the compound of formula (I) is hydrogenated to remove the benzyl in the presence of Pd—C catalyst, and is salified with maleic acid to produce compound (V);

2) upon hydrolysis, compound (V) is converted into silodosin.

The present invention has the following advantages:

(1) Compound (II) organic acid salts of 3-(7-cyano-5-((R)-2-((R)-1-phenylethylamino)propyl)-1-H-indolyl)propyl alcohol (ester or ether), the intermediate of silodosin, provided in the present invention has a high De value and has a high yield in its synthetic method, which simplifies the procedure and thus reduce the cost.

(2) Compound (I) 3-(7-cyano-5-((R)-2-(((R)-1-phenylethyl)(2-(2-(trifluoroethoxy)phenoxy)ethyl)amino)propyl)-1-H-indolyl)propyl alcohol (ester or ether) and its salts, the intermediate of silodosin, provided in the present invention has a high yield in its synthetic method, and avoids the by-product produced in the original techniques which is difficult to separated, and compound (I) reduces the cost and is applicable for industrial production.

DETAILED DESCRIPTION OF EMBODIMENTS

The embodiments of the present invention will be illustrated in more detail in combination with the following examples. The embodiments of the present invention comprise but not limited to the following examples, which should not be deemed as the limitation to the protection scope of the present invention.

EXAMPLE 1

Preparation of 3-(7-cyano-5-(2-oxopropyl)-1-H-indolyl)propyl 4-fluorobenzoate (compound VIII, wherein R is 4-fluorobenzoyl)

150 g (0.365 mol) 3-(7-cyano-5-(2-nitropropyl)-1-H-indolyl)propyl 4-fluorobenzoate (compound VII, wherein R is 4-fluorobenzoyl) was dissolved in 750 mL N,N-dimethyl formamide, and 88.7 g (0.583 mol) 1,8-diazabicyclo[5.4.0]undec-7-ene was added at 0-5° C., into which 118.8 g (1.094 mol) trimethylchlorosilane was then dropped at −15~−10° C. After is dropping, reaction was conducted at −15~−10° C. for 2 h. 66.1 g (0.383 mol) 30% hydrogen peroxide was then dropped into the reaction mixture. After dropping, reaction was conducted for 1 h. The reaction solution was poured into a separating funnel and the supernatant was removed. The reaction solution was then added to 1500 mL 1% sodium sulfite solution at about 10° C., extracted with 1500 mL methyl tertiary ether, and the aqueous phase was extracted with another 750 mL methyl tertiary ether. The combined organic phase was sequentially washed for one time with 750 mL 1mol/L hydrochloric acid, 750 mL saturated sodium bicarbonate, 750 mL water, and 750 mL saturated brine. After drying on sodium sulfate and concentration, an oily substance was obtained (137.6 g). The mass spectrum of the oily substance showed a molecular ion peak wherein [M+1] is 381, HPLC purity is 89.0%.

EXAMPLE 2

Preparation of 3-(7-cyano-5-((R)-2-(R)-1-phenylethylamino)propyl)-1-H-indolyl)propyl-4-fluorobenzoate (compound III, wherein R is 4-fluorobenzoyl)

137.6 g oily substance obtained in Example 1 was dissolved in 1280 mL tetrahydrofuran, and 44.2 g (0.365 mol)

R-(+)-α-phenylethylamine, 1.376 g platinum oxide, and 21.9 g (0.365 mol) acetic acid were added. The reaction mixture was moved to a hydrogenation reactor, and reacted at a temperature of 55° C. and a hydrogen pressure of 8 atmospheric pressure. The reaction was conducted for 27 h. After the reaction was stopped, platinum oxide was filtered, and the filtrate was concentrated under reduced pressure. 1 L ethyl acetate and 1 L saturated brine were added to the concentrate and sodium carbonate was used to adjust the pH value to 7~8. Separated, wherein the aqueous phase was extracted with 500 mL ethyl acetate for one time, and the organic phase was washed with 1 L saturated brine for one time. The combined organic phase was dried on magnesium sulfate and then concentrated to obtain an oily substance (169.6 g). The mass spectrum of the oily substance showed a molecular ion peak wherein [M+1] is 486, HPLC purity is 82.1%.

EXAMPLE 3

Preparation of L-tartaric Acid Salt of 3-(7-cyano-5-((R)-2-((R)-1-phenylethylamino)propyl)-1-H-indolyl)propyl-4-fluorobenzoate (compound II, wherein R is 4-fluorobenzoyl, the Organic Acid is L-tartaric Acid)

84.8 g oily substance obtained in Example 2 was dissolved in 424 mL acetone, and 21.9 g L-tartaric acid (0.150 mol) was added under stirring, the reaction mixture was heated under reflux for 2 h, and then cooled to room temperature to crystallize for 2 h. Subsequently, the reaction mixture was filtered and washed with 80 mL acetone, and then dried in vacuum, to obtain a white solid (64.5 g). The mass spectrum showed a molecular ion peak wherein [M+1] is 486. By calculating from compound VIII, the yield of the three steps is 55.6%. HPLC purity is 99.0%. The de value of (R,R) configuration and (R,S) configuration is 99.1%.

$^1$H NMR spectrum (DMSO-d6): δ ppm 1.0(3H,s), 1.5 (3H,s), 2.0(2H, s), 2.7-3.1(4H, m), 3.4-3.7 (4H, m), 3.9-4.5 (5H, m), 6.7-6.8 (2H, m), 7.1-7.7 (7H, m), 7.9-8.1(2H, m).

EXAMPLE 4

Preparation of R-camphorsulfonic Acid of 3-(7-cyano-5-((R)-2-((R)-1-phenylethylamino)propyl)-1-H-indolyl)propyl-4-fluorobenzoate (Compound II, wherein R is 4-fluorobenzoyl, the Organic Acid is R-camphorsulfonic Acid)

84.8 g oily substance obtained in Example 2 was dissolved in 424 mL dichloromethane, and 34.8 g R-camphorsulfonic acid (0.150 mol) was added under stirring, the reaction mixture was heated under reflux for 2 h, and then cooled to room temperature to crystallize for 2 h. Subsequently, the reaction mixture was filtered and washed with 80 mL dichloromethane, and then dried in vacuum, to obtain a white solid (67.7 g). The mass spectrum showed a molecular ion peak wherein [M+1] is 486. By calculating from compound VIII, the yield of the three steps is 51.7%. HPLC purity is 98.5%. The de value of (R,R) configuration and (R,S) configuration is 96.1%.

$^1$H NMR spectrum (DMSO-d6): δ ppm 1.0 (6H, s), 1.1(3H, s), 1.4(3H,s), 1.6.1-1.9(5H, s), 2.1-2.4 (4H, m), 2.8-3.1(4H, m), 3.4-3.8 (4H, m), 3.9-4.4 (5H, m), 6.7-6.8 (2H, m), 7.1-7.7 (7H, m), 7.9-8.1 (2H, m).

EXAMPLE 5

Preparation of 3-(7-cyano-5-((R)-2-(((R)-1-phenylethyl)(2-(2-(trifluoroethoxy)phenoxy)ethyl)amino)propyl)1-H-indolyl)propyl 4-fluorobenzoate (compound I, wherein R is 4-fluorobenzoyl)

20.0 g (0.031 mol) white solid obtained in Example 3 was dissolved in 100 mL methanol. A saturated sodium carbonate solution was added to adjust the pH value to 9~10. 100 mL ethyl acetate was then used to extract for three times. The organic phase was washed with 100 mL water and 100 mL saturated brine. The combined organic phase was dried on magnesium sulfate and then concentrated to obtain an oily substance. The oily substance was added to the reactor, and then 18.5 g (0.062 mol) compound IV, 10.0 g (0.031 mol) tetrabutylammonium bromide, 12.0 g (0.093 mol) diisopropylethylamine and 20 mL N-methylpyrrolidone were added under stirring, the reaction mixture was heated to 120° C. and reacted for 30 h. After cooling to 100° C., 40 mL toluene and 100 mL water were added and stirred for 10 min. Separated, the aqueous phase was extracted with 40 mL toluene for two times. The organic phase was combined and was sequentially washed with 40 mL 1N hydrochloric acid, 40 mL saturated sodium bicarbonate and 40 mL saturated brine and then was dried on magnesium sulfate. After concentration, the concentrate passed through column chromatography (ethyl acetate: petroleum ether=1:10) to obtain 18.1 g. The mass spectrum showed a molecular ion peak wherein [M+1] is 704, and the yield is 83.2%.

$^1$H NMR spectrum (DMSO-d6): δ ppm 0.8 (3H, s), 1.2 (3H, m), 2.0 (2H, m), 2.1-2.3 (1H, m), 2.7-3.0(4H, m), 3.3 (2H, s), 3.4-3.5 (2H, m), 3.5-3.6 (2H,s), 3.8-4.1 (3H, m), 4.3 (2H, s), 4.5-4.7 (2H, m), 6.7 (2H, s), 6.8-6.9 (2H, m), 6.9-7.0(1H, m), 7.0-7.1(1H, m), 7.1-7.3 (7H, m), 7.9-8.1 (2H, s).

EXAMPLE 6

Preparation of 3-(7-cyano-5-((R)-2-(((R)-1-phenylethyl)(2-(2-(trifluoroethoxy)phenoxy)ethyl)amino)propyl)1-H-indolyl)propyl 4-fluorobenzoate (compound I, wherein R is 4-fluorobenzoyl)

20.0 g (0.031 mol) white solid obtained in Example 3 was dissolved in 100 mL methanol. A saturated sodium carbonate solution was added to adjust the pH value to 9-10. 100 mL ethyl acetate was then used to extract for three times. The organic phase was washed with 100 mL water and 100 mL saturated brine. The combined organic phase was dried on magnesium sulfate and then concentrated to obtain an oily substance. The oily substance was added to the reactor, and then 18.5 g (0.062 mol) compound IV, 10.0 g (0.031 mol) tetrabutylammonium bromide, 12.0 g (0.093 mol) diisopropylethylamine were added under stirring, the reaction mixture was heated to 120° C. and reacted for 24 h in the absence of solvent. After cooling to 100° C., 40 mL toluene and 100 mL water were added and stirred for 10 min. Separated, the aqueous phase was extracted with 40 mL toluene for two times. The organic phase was combined and was sequentially washed with 40 mL 1N hydrochloric acid, 40 mL saturated sodium bicarbonate and 40 mL saturated brine and then was dried on magnesium sulfate. After concentration, an oily substance (32.3 g) was obtained. The mass spectrum showed a molecular ion peak wherein [M+1] is 704, HPLC purity is 79.1%.

EXAMPLE 7

Preparation of 3-(7-cyano-5-((R)-2-(((R)-1-phenyl-ethyl)(2-(2-(trifluoroethoxy)phenoxy)ethyl)amino)propyl)1-H-indolyl)propyl 4-fluorobenzoate (compound I, wherein R is 4-fluorobenzoyl)

20.0 g (0.031 mol) white solid obtained in Example 3 was dissolved in 100 mL methanol. A saturated sodium carbonate solution was added to adjust the pH value to 9-10. 100 mL ethyl acetate was then used to extract for three times. The organic phase was washed with 100 mL water and 100 mL saturated brine. The combined organic phase was dried on magnesium sulfate and then is concentrated to obtain an oily substance. The oily substance was added to the reactor, and then 18.5 g (0.062 mol) compound IV, 8.2 g (0.031 mol) 18-crown-6, 16.4 g (0.155 mol) sodium carbonate and 15 mL N-methylpyrrolidone were added under stirring, the reaction mixture was heated to 120° C. and reacted for 24 h. After cooling to 100° C., 40 mL toluene and 100 mL water were added and stirred for 10 min. Separated, the aqueous phase was extracted with 40 toluene for two times. The organic phase was combined and was sequentially washed with 40 mL 1 N hydrochloric acid, 40 mL saturated sodium bicarbonate and 40 mL saturated brine and then was dried on magnesium sulfate. After concentration, an oily substance (31.5 g) was obtained. The mass spectrum showed a molecular ion peak wherein [M+1] is 704, HPLC purity is 79.5%.

EXAMPLE 8

Preparation of 3-(7-cyano-5-((R)-2-(((R)-1-phenyl-ethyl)(2-(2-(trifluoroethoxy)phenoxy)ethyl)amino)propyl)1-H-indolyl)propyl alcohol (compound I, wherein R is H)

20.0 g (0.028 mol) white solid obtained in Example 4 was dissolved in 100 mL methanol, and NaOH solution was added to adjust the pH value to 13. The reaction was conducted for a half hour. Subsequently, 100 mL ethyl acetate was used to extract for 3 times. The organic phase was washed with 100 mL water and 100 mL saturated brine. After drying on magnesium sulfate and concentration, an oily substance (9.8 g) was obtained as 3-(7-cyano-5-((R)-2-((R)-1-phenylethylamino)propyl)1-H-indolyl)propyl alcohol (compound II, wherein R is H). The oily substance was added to the reactor, and then 16.7 g (0.056 mol) compound IV, 9.0 g (0.028 mol) tetrabutylammonium bromide, 10.8 g (0.084 mol) diisopropylethylamine and 15 mL N-methylpyrrolidone were added under stirring, the reaction mixture was heated to 120° C. and reacted for 40 h. After cooling to 100° C., 40 mL toluene and 100 mL water were added and stirred for 10 min. Separated, the aqueous phase was extracted with 40 toluene for two times. The organic phase was combined and was sequentially washed with 40 mL 1N is hydrochloric acid, 40 mL saturated sodium bicarbonate and 40 mL saturated brine and then was dried on magnesium sulfate. After concentration, the concentrate passed through column chromatography (ethyl acetate: petroleum ether=1:10) to obtain 12.2 g. The mass spectrum showed a molecular ion peak wherein [M+1] is 582, and the yield is 75.2%.

$^1$H NMR spectrum (DMSO-d6): δ ppm 0.8 (3H, s), 1.2-1.3 (3H, m), 2.0-2.1 (2H, m), 2.2-2.3 (2H, m), 2.8-3.0 (4H, m), 3.3 (2H, s), 3.4-3.6 (2H, m), 3.6-3.7 (2H, s), 3.9-4.1 (3H, m), 4.3 (2H, s), 4.5-4.6 (2H, m), 6.7 (2H, s), 6.9-7.1 (1H, m), 7.1-7.2 (1H, m), 7.2-7.4 (7H, m).

EXAMPLE 9

Preparation of Maleic Acid Salt of 3-(5-((R)-2-(2-(2-(2,2,2-trifluoroethoxy)phenoxy)ethylamino)propyl)-7-H-cyano-1-indolyl)propyl 4-fluorobenzoate (compound V, wherein R is 4-fluorobenzoyl)

32.3 g oily substance obtained in Example 6 was dissolved in 320 mL methanol and 6.5 g Pd—C was added. The reaction mixture was reacted under 1 atmospheric pressure H2 at 65° C. for 4 h. Filtered and concentrated, 100 mL water was added and extracted with 100 mL ethyl acetate for 3 times. The organic phase was combined and washed with 100 mL saturated brine for 1 time, dried on magnesium sulfate and then concentrated. The concentrate was then dissolved in 60 mL tetrahydrofuran, into which 120 mL isopropyl ether and 3.16 g (0.027 mol) maleic acid were added. The solution was heated under reflux for 10 min, and then naturally cooled to room temperature. Subsequently, cooled to 0-10° C. for crystallization, 180 mL isopropyl ether was further added to continue to crystallize for 2 h. Filtered and dried to obtain a white solid (16.0 g). By calculating from compound II, the yield of the two steps is 71.9%. The mass spectrum showed a molecular ion peak wherein [M+1] is 600. HPLC purity is 98.0%, and ee value is 99.5%.

$^1$ H NMR spectrum (DMSO-d6): δ ppm 1.1-1.2(3H, d), 2.0-2.1(2H, m), 2.5-2.6(1H, dd), 2.8-2.9 (2H, t), 2.96-3.0 (1H, dd), 3.3-3.5 (3H, m), 3.5-3.7(4H, m),4.2-4.3 (2H, t), 4.3-4.4 (2H, t), 4.6-4.7 (2H, m), 4.8-5.2 (1H, m), 6.9-7.2 (6H, m), 7.3-7.4 (2H, m), 8.0-8.1 (2H, m).

EXAMPLE 10

Preparation of Compound (VI)

16.0 g (0.0244 mol) solid obtained in Example 9 was dissolved in 200 mL DMSO, 24.0 mL 5 mol/L NaOH was added, and then 14.0 g 30% hydrogen peroxide was slowly dropped at 18~20° C. The reaction mixture was reacted at 25~30° C. for 4 h. 200 mL water was added, and extracted with 100 mL ethyl acetate for 3 times. The organic phase was combined, into which 60 mL 2 mol/L hydrochloric acid was added and stirred for 15 min. Separated, the organic phase was further extracted with 30 mL 2 mol/L hydrochloric acid for 2 times. The aqueous phase was combined and then saturated sodium carbonate solution was added to adjust the pH value to 9~10. Extracted with 100 mL ethyl acetate for 3 times, and the organic phase was combined and washed with 30 mL saturated NaCl aqueous solution for 1 time, and then dried on magnesium sulfate. After concentration, the concentrate was further dissolved in ethyl acetate, naturally cooled until crystallization, filtered and dried to obtain a white solid (10.0 g). The mass spectrum showed a molecular ion peak wherein [M+1] is 496, the yield is 82.8%, and HPLC purity is 99.0%.

$^1$ H NMR spectrum (DMSO-d6): δ ppm 0.9-1.0 (3H, d), 1.5-1.6 (1H, s), 1.6-1.7 (2H, m), 2.3-2.4 (1H, t), 2.6-2.7 (1H, dd), 2.8-3.0 (5H, m), 3.2-3.2 (2H, m), 3.3-3.4 (2H, m), 3.4-3.5 (2H, t), 4.0-4.1 (2H, t), 4.2-4.3 (1H, brs), 4.6-4.8 (2H, t), 6.9-7.15 (6H, m), 7.2-7.3 (1H, brs), 7.5-7.6 (1H, s).

COMPARATIVE EXAMPLE

Preparation of Compound (4) in the Route in Patent CN101993406

82.0 g compound (III) in Example 2 was dissolved in 600 mL methanol, to and 56 mL 3 mol/L HCl was added under stirring. After uniformly stirring, 14.0 g (7.0%) Pd—C was added at 2-10 atmospheric pressure. The reaction is conducted at 40-80° C. After the reaction is over, the Pd—C was removed by filtering. After concentration, the concentrate was dissolved in 300 mL dichloromethane. Water was added and extracted, and then dried on anhydrous is sodium sulfate. After filtering and concentration, 65 g oily substance was obtained. The oily substance was heated and dissolved in 180 mL acetone, into which L-tartaric acid aqueous solution [25.3 g+90 g water] was dropped at 40° C. After dropping, the mixture was heated and dissolved under reflux, and then naturally cooled to 15° C. and stirred for 2 h. The solid was filtered and dissolved with acetone/water (170 mL:170 mL) under reflux, and cooled to 30° C. to crystallize for 3 h. Subsequently, the solid was filtered and dissolved with acetone/water (140 mL:140 mL) under reflux, and cooled to 30° C. to crystallize for 3 h. Subsequently, the solid was filtered and dissolved with acetone/water (140 mL:140 mL) under reflux, and cooled to 30° C. to crystallize for 3 h. Subsequently, the solid was filtered and dried to obtained 30.0 solid (33.4%), and ee value is 93.9%.

NMR spectrum (DMSO-d6): δ ppm 1.0-1.2 (3H, d), 2.0-2.2 (2H, m), 2.6-2.8 (2H, m), 2.9-3.0 (3H, m), 3.2-3.4 (2H, m), 3.4-3.5(1H, m), 3.5-3.6 (2H, t), 3.6-3.7 (2H, m), 3.9-4.0 (2H, t), 4.3-4.4 (2H, t), 6.9-7.1 (2H, m), 7.2-7.4 (2H, m), 7.9-8.1 (2H, m).

What is claimed is:

1. A compound as represented by formula (I),

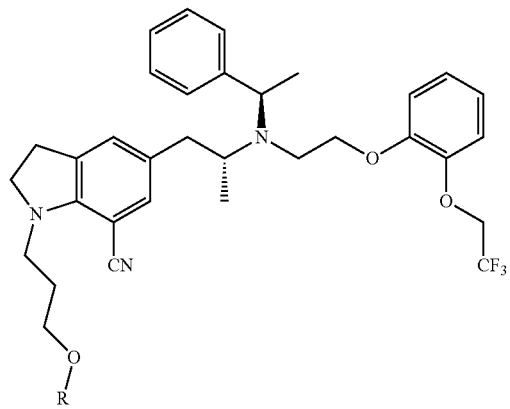

(I)

or a pharmaceutically acceptable salt thereof, wherein, R is selected from H, formyl, aliphatic acyl, substituted or unsubstituted aromatic formyl, tetrahydropyranyl, and trialkylsilicyl.

2. The compound of claim 1, wherein R is 4-fluorobenzoyl.

3. An intermediate compound for synthesizing compound (I) of claim 1, as represented by structural formula (II),

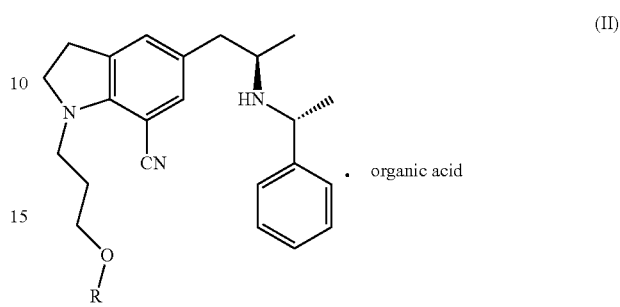

(II)

wherein R is selected from H, formyl, aliphatic acyl, substituted or unsubstituted aromatic formyl, tetrahydropyranyl and trialkylsilicyl, and the organic acid is selected from L-dibenzoyl tartaric acid, L-lactic acid, L-malic acid, R-camphorsulfonic acid, S-mandelic acid, N-carbobenzoxy-L-phenylalanine, and L-tartaric acid.

4. A method of preparing compound (I), wherein:
a) compound (III) is reacted with an organic acid in an organic solvent to produce compound (II),
b) compound (II) and compound (IV) are reacted in the presence of phase transfer catalyst and base and in the presence or absence of an organic solvent, to produce compound (I)

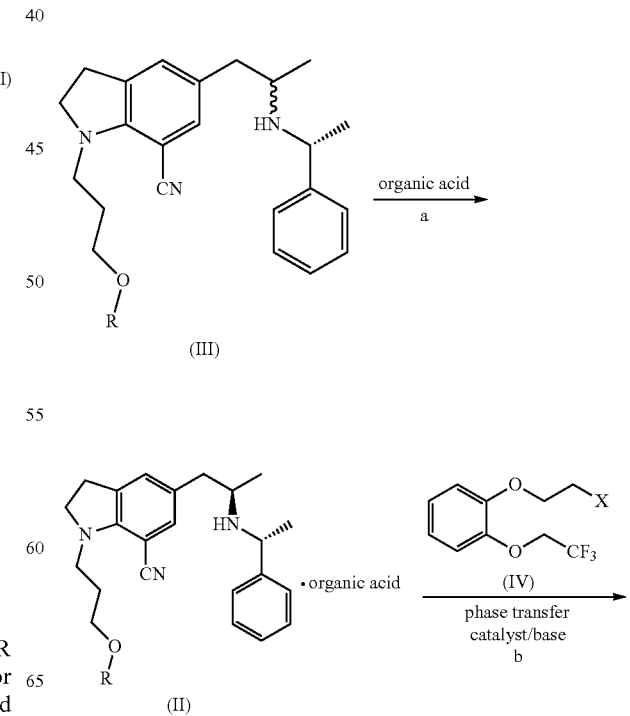

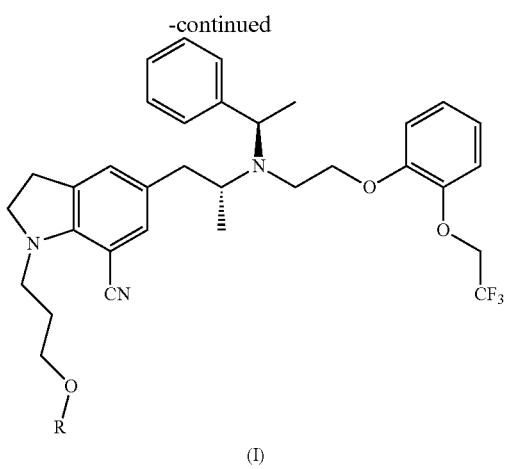

(I)

wherein R is selected from H, formyl, aliphatic acyl, substituted or unsubstituted aromatic tetrahydropyranyl, and trialkylsilicyl.

5. The method of claim 4, wherein the organic acid in step a) is selected from L-dibenzoyl tartaric acid, L-lactic acid, L-malic acid, R-camphorsulfonic acid, S-mandelic acid, N-carbobenzoxy-L-phenylalanine, and L-tartaric acid.

6. The method of claim 4, wherein the organic solvent in step a) is a single organic solvent selected from dichloromethane, acetone, butanone, ethyl acetate, methanol, ethanol, isopropanol, acetonitrile, tetrahydrofuran, methyl tertiary ether, isopropyl ether, and the reaction temperature is 0~80° C.

7. The method of claim 4, wherein, when an organic solvent is present, the organic solvent in step b) is selected from acetonitrile, toluene, xylene, N,N-dimethyl acetamide, N,N-dimethyl formamide, and N-methyl pyrrolidone.

8. The method of claim 4, wherein the phase transfer catalyst in step b) is selected from a quaternary ammonium salt or a crown ether, and the amount of the catalyst is 0.1-2.0 times of the molar weight of the compound (II) to which the catalyst is reacted with.

9. The method of claim 8, wherein the phase transfer catalyst in step b) is selected from tetrabutylammonium bromide, tetrabutylammonium chloride, tetrabutylammonium hydrogen sulfate, 18-crown-6, and 15-crown-5.

10. The method of claim 4, wherein the base in step b) is inorganic base or organic base, wherein the inorganic base is selected from potassium hydroxide, sodium hydroxide, sodium bicarbonate, potassium bicarbonate, potassium carbonate, and sodium carbonate; the organic base is selected from diisopropyl ethyl amine, triethylamine, 1,8-diazabicyclo[5.4.0]undec-7-ene, and pyridine.

11. A method of preparing silodosin comprising:
1) hydrogenating compound (I) to remove the benzyl in the presence of Pd-C catalyst, and is salified with maleic acid to produce compound (V);
2) hydrolyzing compound (V) to produce compound (VI);

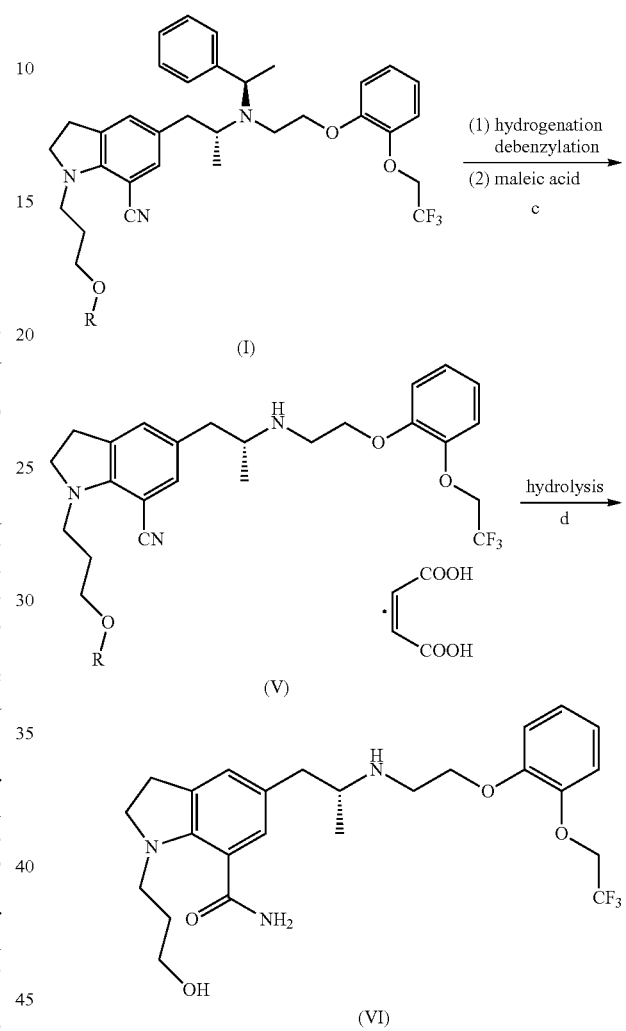

wherein R is selected from H, formyl, aliphatic acyl, substituted or unsubstituted aromatic formyl, tetrahydropyranyl, and trialkylsilicyl.

* * * * *